United States Patent
Palazzolo et al.

(10) Patent No.: US 9,427,715 B2
(45) Date of Patent: Aug. 30, 2016

(54) BONE CEMENT MIXING AND DELIVERY SYSTEM AND METHODS OF USE THEREOF

(75) Inventors: Robert Palazzolo, Boxborough, MA (US); Manish Sutaria, Watertown, MA (US); Aliassghar N. Tofighi, Waltham, MA (US); Tak L. Chang, Boxborough, MA (US); Aron D. Rosenberg, Brighton, MA (US)

(73) Assignee: ETEX Corporation, Cambridge, MA (US)

( * ) Notice: Subject to any disclaimer, the term of this patent is extended or adjusted under 35 U.S.C. 154(b) by 1114 days.

(21) Appl. No.: 12/675,455

(22) PCT Filed: Aug. 28, 2008

(86) PCT No.: PCT/US2008/010214
§ 371 (c)(1),
(2), (4) Date: Jan. 25, 2011

(87) PCT Pub. No.: WO2009/032173
PCT Pub. Date: Mar. 12, 2009

(65) Prior Publication Data
US 2011/0112543 A1    May 12, 2011

Related U.S. Application Data

(60) Provisional application No. 60/966,579, filed on Aug. 29, 2007.

(51) Int. Cl.
*A61B 17/88* (2006.01)
*B01F 15/02* (2006.01)
(Continued)

(52) U.S. Cl.
CPC ........... *B01F 15/0201* (2013.01); *B01F 5/0685* (2013.01); *B01F 5/0688* (2013.01); *B01F 11/0071* (2013.01); *B01F 15/0225* (2013.01); *A61B 17/8827* (2013.01)

(58) Field of Classification Search
CPC .............. A61M 2039/1083; A61M 2039/1088
USPC ...................................... 606/92–94
See application file for complete search history.

(56) References Cited

U.S. PATENT DOCUMENTS 3,770,026 A * 11/1973 Isenberg ........... A61M 5/31525
                                          141/2
4,551,135 A * 11/1985 Gorman et al. ................. 604/82
(Continued)

FOREIGN PATENT DOCUMENTS

WO    WO 2005/069837      8/2005
WO    WO2009/032173 A1    3/2009

OTHER PUBLICATIONS

International Search Report and Written Opinion for PCT/US08/10214, mailed Nov. 25, 2008.
(Continued)

*Primary Examiner* — Samuel Hanna
(74) *Attorney, Agent, or Firm* — Schwegman Lundberg & Woessner, P.A.

(57) ABSTRACT

Bone cement mixing and delivery device and methods are disclosed. The device includes a first tube/barrel (e.g., a syringe barrel) containing a bone cement powder and a second tube/barrel that can be filled with or that contains a liquid; the first and second tubes/barrels can be fluidly connected end-to-end such that there is fluid communication between the tubes/barrels. Also disclosed are methods of preparing the device for use, methods for forming a bone cement using the device, and methods and device design to extend the shelf life of the device.

11 Claims, 2 Drawing Sheets

Disassembled view of mixing device components

Mixing device as packaged with bone cement powder, connector, and porous cap.

(51) Int. Cl.
*B01F 5/06* (2006.01)
*B01F 11/00* (2006.01)

(56) References Cited

U.S. PATENT DOCUMENTS

| | | | | |
|---|---|---|---|---|
| 4,671,263 | A | * | 6/1987 | Draenert .................. 606/94 |
| 4,743,229 | A | * | 5/1988 | Chu .................. A61F 2/4644 604/110 |
| 4,919,153 | A | | 4/1990 | Chin |
| 4,973,168 | A | * | 11/1990 | Chan .................. 366/139 |
| 5,181,918 | A | * | 1/1993 | Brandhorst et al. ............ 606/92 |
| 5,226,877 | A | | 7/1993 | Epstein |
| 5,476,880 | A | * | 12/1995 | Cooke et al. ................. 523/115 |
| 5,902,839 | A | * | 5/1999 | Lautenschlager et al. ... 523/115 |
| 6,572,256 | B2 | * | 6/2003 | Seaton et al. ................. 366/139 |
| 6,709,149 | B1 | | 3/2004 | Tepic |
| 7,837,733 | B2 | * | 11/2010 | Collins et al. ............ 623/17.12 |
| 2001/0016703 | A1 | | 8/2001 | Wironen et al. |
| 2002/0101785 | A1 | | 8/2002 | Edwards et al. |
| 2003/0078589 | A1 | * | 4/2003 | Preissman .................. 606/93 |
| 2003/0120351 | A1 | * | 6/2003 | Tofighi et al. ............. 623/23.62 |
| 2003/0225378 | A1 | | 12/2003 | Wilkie et al. |
| 2004/0049203 | A1 | * | 3/2004 | Scribner et al. ................ 606/93 |
| 2004/0071668 | A1 | * | 4/2004 | Bays .................. A61F 2/00 424/93.7 |
| 2005/0209555 | A1 | * | 9/2005 | Middleton et al. ............. 604/82 |
| 2006/0052794 | A1 | * | 3/2006 | McGill et al. ................. 606/93 |
| 2006/0100587 | A1 | * | 5/2006 | Bertron ................ A61M 5/284 604/191 |
| 2006/0264967 | A1 | | 11/2006 | Ferreyro et al. |
| 2007/0016215 | A1 | * | 1/2007 | Wilander et al. .............. 606/93 |
| 2007/0026030 | A1 | | 2/2007 | Gill et al. |
| 2007/0185495 | A1 | | 8/2007 | Hess et al. |
| 2008/0214998 | A1 | * | 9/2008 | Kurek et al. ............... 604/93.01 |

OTHER PUBLICATIONS

International Preliminary Report on Patentability for PCT/US08/10214, issued on Mar. 2, 2010 and mailed on Mar. 11, 2010.
Extended European Search Report for EP 08829040.8 dated Jan. 26, 2011.
Office Action for Application No. AU2008296990, dated Mar. 5, 2013 (5 pages).
Patent Examination Report No. 2 in Australian Patent Application No. 2008296990 issued Apr. 2, 2014 (5 pages).
"Australian Application Serial No. 2008296990, Subsequent Examiner Report mailed Nov. 18, 2014", 3 pgs.
"Canadian Application Serial No. 2,698,017, Office Action mailed Jul. 10, 2014", 2 pgs.
"European Application Serial No. 08829040.8, Examination Notification Art. 94(3) mailed Oct. 4, 2011", 3 pgs.
"European Application Serial No. 08829040,8, Examination Notification Art. 94(3) mailed Nov. 13, 2012", 4 pgs.
"European Application Serial No. 08829040.8, Office Action mailed Feb. 14, 2011", 1 pg.
"European Application Serial No. 08829040,8, Office Action mailed Apr. 28, 2010", 2 pgs.
"European Application Serial No. 08829040.8, Office Action mailed Dec. 6, 2013", 7 pgs.
"European Application Serial No. 08829040.8, Response filed Apr. 16, 2012 to Examination Notification Art. 94(3) mailed Oct. 4, 2011", 11 pgs.
"European Application Serial No. 08829040.8, Response filed May 13, 2013 to Examination Notification Art. 94(3) mailed Nov. 13, 2012", 10 pgs.
"European Application Serial No. 08829040.8, Response filed Jun. 7, 2010 to Office Action mailed Apr. 28, 2010", 5 pgs.
"European Application Serial No. 08829040.8, Response filed Aug. 22, 2011 to Office Action mailed Feb. 14, 2011", 18 pgs.

* cited by examiner

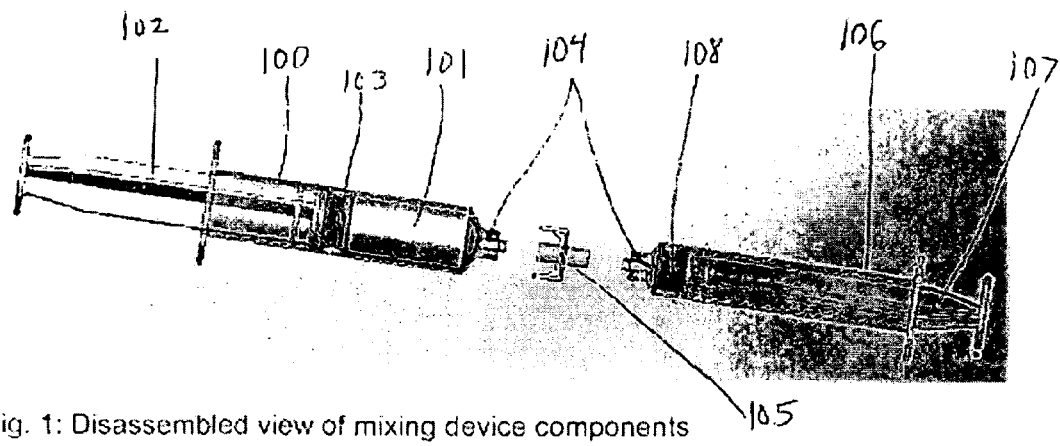
Fig. 1: Disassembled view of mixing device components
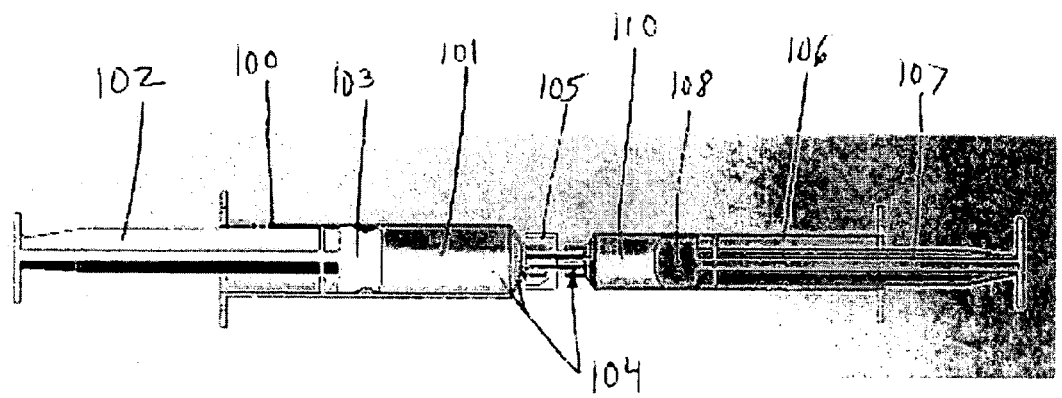
Fig. 2: Sectional view of connected mixing and delivery device
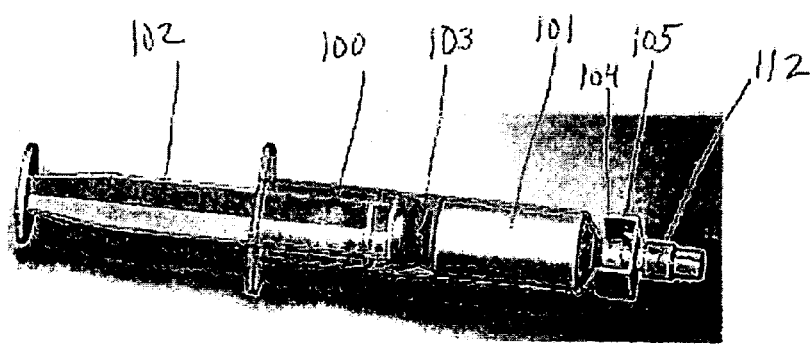
Fig. 3: Mixing device as packaged with bone cement powder, connector, and porous cap.

BONE CEMENT MIXING AND DELIVERY SYSTEM AND METHODS OF USE THEREOF

CROSS-REFERENCE TO RELATED APPLICATIONS

This application claims priority under 35 U.S.C. §371 from international application PCT/US2008/010214, filed Aug. 28, 2008, which claims priority under 35 U.S.C. §119 from provisional application No. 60/966,579, filed Aug. 29, 2007. Both of these applications are incorporated by reference herein in their entirety.

FIELD OF THE INVENTION

The present invention relates to bone cement mixing devices, related systems, and methods of use thereof.

BACKGROUND OF THE INVENTION

Bone cements are used in orthopedic procedures for filling bone voids and repairing defects. They typically comprise a cement powder that is mixed with a liquid and manually applied to the defect site. The mixed cement may also be transferred into a delivery device and injected into the site. Current mixing and delivery systems rely on manual open mixing, such as a bowl and spatula, which can be messy and difficult to achieve uniformity. The open mixing and transfer steps also present contamination risk. Furthermore, the transfer step is messy and time consuming. Thus, there is a need for a better bone cement mixing and delivery system.

SUMMARY OF THE INVENTION

The present invention features an enclosed bone cement mixing and delivery system. The present mixing and delivery system is based on syringe-to-syringe mixing, which eliminates the open mixing and transfer steps and reduces contamination risk and preparation time. The system also improves cement injectability and includes a packaging design that promotes powder filling and extends shelf life.

Accordingly, the invention features a mixing and delivery system that includes first and second rigid tubes containing movable pistons, in which the tubes are joined end-to-end such that there is communication between the tubes that allows fluid to move between the tubes, and wherein at least one of the tubes includes a bone cement powder. The application of force to alternate pistons produces high shear during the mixing step. In one embodiment, the tubes and pistons are provided as disposable syringes. In yet another embodiment, the syringes have Luer tips. The pistons are capable of moving independent of one another.

Bone cement powder is filled into one of the two tubes. In one embodiment, the powder is a calcium phosphate composition. In preferred embodiments, the calcium phosphate composition includes amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, or tricalcium phosphate, or mixtures thereof. Alternatively, the calcium phosphate composition includes an amorphous calcium phosphate and a second calcium phosphate source, e.g., poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, or tricalcium phosphate, or mixtures thereof. In other embodiments, the calcium phosphate composition is a powder described in or prepared according to the methods disclosed in, e.g., U.S. Pat. No. 5,650,176, U.S. Pat. No. 5,783,217, U.S. Pat. No. 6,214,368, U.S. Pat. No. 6,027,742, U.S. Pat. No. 6,214,368, U.S. Pat. No. 6,287,341, U.S. Pat. No. 6,331,312, U.S. Pat. No. 6,541,037, U.S. Patent Application Publication No. 2003/0120351, U.S. Patent Application Publication No. 20040097612, U.S. Patent Application Publication No. 2005/0084542, U.S. Patent Application Publication No. 2007/0128245, and WO 2005/117919, all of which are incorporated herein by reference.

In other embodiments, the calcium phosphate composition has an average crystalline domain size of less than 100 nm (e.g., in the range of between about 1 nm to about 99 nm; preferably 50 nm or less; more preferably 10 nm or less). In another embodiment, the calcium phosphate composition has a tap density of between about 0.5 g/cm$^3$ to about 1.5 g/cm$^3$, preferably the calcium phosphate composition has a tap density of greater than about 0.7 g/cm$^3$ (e.g., about 1.0 g/cm$^3$).

In another embodiment, the calcium phosphate composition includes a supplemental material, e.g., a biocompatible cohesiveness agent or a biologically active agent (see, e.g., the biocompatible cohesiveness agents and biologically active agents as described and defined in U.S. Patent Application Publication No. 2007/0128245; incorporated hereby by reference). In yet another preferred embodiment, the biocompatible cohesiveness agent is present in the calcium phosphate composition in an amount in the range of about 0.5 wt % to about 20 wt % (e.g., less than about 20 wt %, preferably less than about 10 wt %, more preferably less than about 5 wt %, and most preferably less than about 1 wt %).

In another embodiment, the powder is compressed to a desired density to enhance the wetting characteristics, optimize mixing forces, and minimize the amount of air in the mixed product. In a preferred embodiment, the powder has a density in the range of about 0.1 to about 1.2 g/cc, preferably, 0.5, 0.6, 0.7, 0.8, 0.9, 1.0, 1.1, or 1.2 g/cc, and most preferably 1.0 g/cc. In another embodiment; the tube with powder has an affixed porous cap to aid powder filling and compaction by venting air; the porous cap allows air to escape from the tube, but prevents escape of the powder. In preferred embodiments, the porous cap has pores that are less than or equal to 1.0 mm in diameter, preferably less than or equal to 750, 500, 300, 250, 150, and 100 μm in diameter, and more preferably less than 75, 50, 25, 15, 10, and 5 μm in diameter, and most preferably less than or equal to 1, 0.5, 0.4, 0.3, 0.2, 0.1, and 0.05 μm in diameter. The cap also allows released moisture to exit the device, which extends shelf life and long term stability of the powder during storage by preventing degradation of the powder components. In another embodiment, the cap is composed of a porous polymer, ceramic, or metal material.

The second tube is filled with a liquid. In an embodiment, the liquid is a physiologically-acceptable fluid including but are not limited to water, saline, and phosphate buffers. In other embodiments, the fluid can be a biological fluid, e.g., any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. In a preferred embodiment, the calcium phosphate composition, once hydrated, forms a paste. Varying amounts of a liquid may be added to the powder to produce a paste having one or more desired characteristics. For example, in at least some embodiments, 0.3-2.0 cc of liquid per gram of powder is used to prepare a paste that is formable, i.e., capable of being molded and retaining its shape. In at least some embodiments, the paste is injectable, i.e., capable of passing through a 16- to 18-gauge needle. The paste can also be prepared for delivery through a catheter (e.g., a catheter having a 7-15 gauge needle, and more preferably a 7, 8, 9, 10, 11, 12, 13, 14, or 15 gauge needle).

The powder-containing tube and the liquid-containing tube can be joined end-to-end such that there is communication between the tubes that allows fluid to move between the tubes. In an embodiment, the tubes are joined using a Luer connector, which provides a tight seal to prevent leakage and contamination.

Mixing of the powder and liquid is initiated by pressing a piston in the liquid-containing tube, which forces the liquid through the connection into the powder present in the powder-containing tube. The liquid is allowed to soak into the powder. Preferably, the liquid is allowed to soak into the powder for 1, 2, 3, 4, 5, 10 seconds, preferably 30 seconds or 1, 2, 3, 4, or 5 minutes, or more preferably 10, 15, 20, or 30 minutes. Following the soak period, gas may be entrapped within the material. In preferred embodiments, the gas is selected from carbon dioxide, air, nitrogen, helium, oxygen, and argon. The gas can be removed by disconnecting the two tubes and repositioning the pistons until all gas is expelled, keeping the solid and liquid content within the tubes. This venting step improves the mixing and mechanical properties of the material. The two tubes are reconnected after venting the gas.

Mixing is resumed by alternately applying pressure to the pistons present in the tubes to transfer the hydrated and unhydrated material through the connector from one tube to the other. In a preferred embodiment, mixing continues until the material is substantially completely hydrated. If all material does not transfer, the material is alternately pressed back and forth between tubes until it all flows and is uniformly hydrated and mixed. In a preferred embodiment, the orifice formed from the joining of the two tubes is sized such that it breaks agglomerates and renders the cement more injectable. In several embodiments, the orifice is 5.0, 4.0, 3.0, 2.0, or 1.0 mm in diameter, preferably the orifice is 0.9, 0.8, 0.7, 0.6, 0.5, 0.4, 0.3, 0.2, or 0.1 mm in diameter.

When mixing is completed (e.g., after approximately 3, 4, 5, 6, 7, 8, 9, 10, 15, 20, or 30 or more depressions), the hydrated material, which is preferably in a paste form, is dispensed substantially completely into one of the two tubes for delivery. At this time, the second tube is disconnected from the first tube. In a preferred embodiment, one of the two tubes used for mixing is a delivery syringe, which is used to deliver the hydrated powder material once it is substantially mixed (e.g., to a site in a human patient requiring bone cement). A delivery tip, such as a needle, can be attached to the end of the delivery syringe to deliver the material (e.g., using a Luer connector). In a preferred embodiment, the substantially completely mixed and hydrated material is sterile.

In an embodiment, the calcium phosphate material, after hydration and hardening, has a porosity of about 5%, more preferably the material is about 10, 20, or 30% porous, and most preferably the material is about 40, 50, or 60% porous. In a preferred embodiment, the calcium phosphate material is at least about 20% porous. In other embodiments, the hydrated material has a Ca/P ratio of less than 1.67. In particularly preferred embodiments, the hydrated material is a paste that hardens to form a calcium phosphate having an overall Ca/P molar ratio in the range of 1.0-1.67, preferably 1.3-1.65, more preferably 1.4-1.6, and most preferably close to that of naturally-occurring bone, that is in the range of 1.45 to 1.67. In a preferred embodiment, the hardened calcium phosphate composition has a Ca/P molar ratio of equal to or less than about 1.5.

In yet other embodiments, the hardened calcium phosphate composition exhibits a compressive strength of equal to or greater than about 1 or 2 MPa. In other embodiments, the compressive strength is in the range of about 1 MPa to about 150 MPa (e.g., 20, 30, 40, 50, 60, 70, 80, 90, or 100 MPa). In yet other embodiments, the compressive strength is 120 MPa or greater (e.g., 120 to 150 MPa). In another embodiment, the compressive strength is in the range of about 20-30 MPa.

A second aspect of the invention features a method of bone repair that includes administering the hydrated material prepared using the mixing system of the first aspect of the invention. In an embodiment, the hydrated material is a formable, self-hardening, paste, which is moldable and cohesive when applied to an implant site in vivo, and hardens to form a calcium phosphate composition. In at least some embodiments, the paste hardens to form a calcium phosphate composition (e.g., a poorly crystalline apatitic (PCA) calcium phosphate) having significant compressive strength. The hydrated material may be implanted in vivo in paste form or as a hardened calcium phosphate. The composition can be used to repair bone, e.g., damaged bone, or as a delivery vehicle for biologically active agents. All of the embodiments of the first aspect of the invention apply to the composition utilized in the method of the second aspect of the invention.

As used herein, the term "about" means±10% of the recited value.

As used herein, the term "substantial" or "substantially" means sufficiently to accomplish one or more of the goals, applications, functions and purposes described herein. For example, "substantially mixed" means that one or more powder components used in conjunction with the mixing devices of the invention are mixed with one or more other components (one or more of which may be an aqueous fluid) to near homogeneity such that the mixture is relatively or nearly uniform in composition. In an embodiment, the mixture forms a slurry, paste, or cement, and is injectable.

BRIEF DESCRIPTION OF THE DRAWINGS

The invention is described with reference to the following figures, which are presented for the purpose of illustration only and which are not intended to be limiting of the invention.

FIG. 1 is a plan view of the packaged device with powder and porous cap.

FIG. 2 is a disassembled view of the mixing and delivery system.

FIG. 3 is a cross section of the mixing device assembly.

DETAILED DESCRIPTION

Structure

Figure 4:
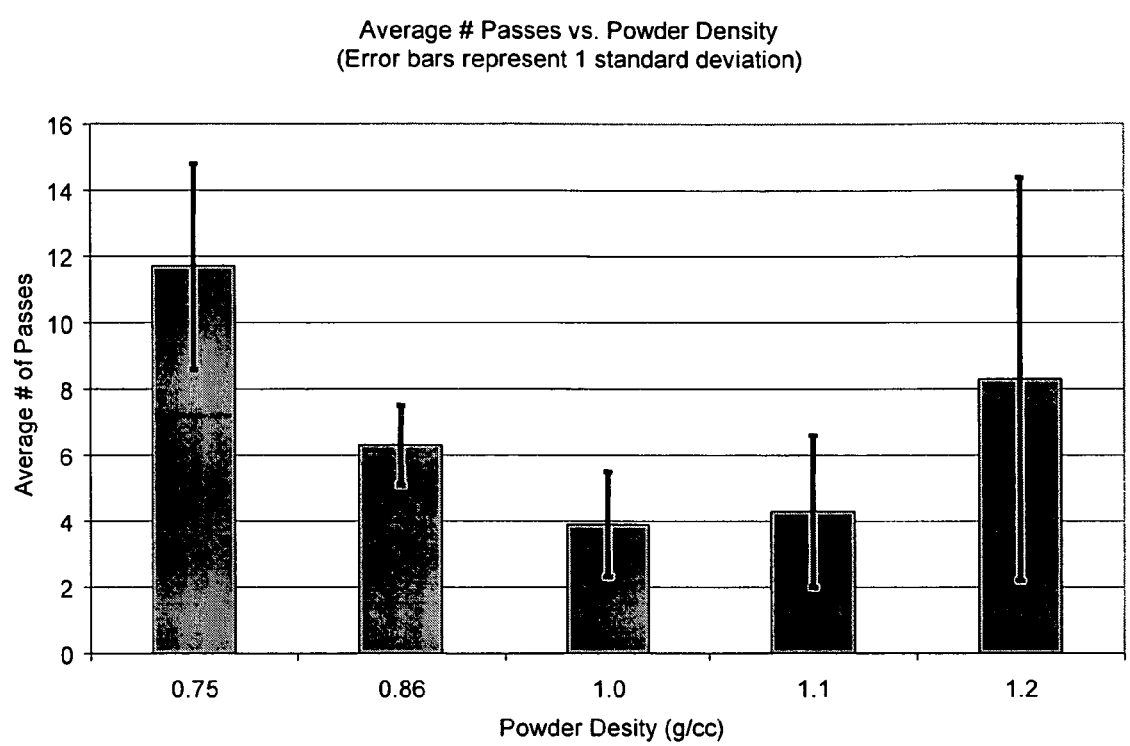
FIG. 4 is a graph showing the average number of passes/strokes used to hydrate 6.0 grams of a calcium phosphate compressed to the indicated density with 3.0 cc of saline using the mixing device of the invention.

Referring to FIG. 1, powder 101 is filled into barrel 100 and compressed to occupy a desired density (e.g., between 0.1 g/cc and 1.1 g/cc) within barrel 100 and stopper 103. Luer connector 105 is attached to tip 104, and porous cap 112 is attached to Luer connector 105. This device may be packaged within a moisture barrier configuration along with desiccant as preservative (not shown). A desiccant is defined as any material with an affinity for moisture higher than that of the protected product; examples include but are not limited to clay, silica gel, or molecular sieve.

Referring to FIGS. 2 and 3, barrel 100 contains powder 101 and a movable plunger 102. While disassembled, a second barrel 106 can be filled with liquid 110 by retracting movable plunger 107. Rubber stoppers 103 and 108 prevent leakage of contents from the barrels. Barrels 100 and 106 have Luer fittings 104 which are connected using Luer connector 105, which provides a leak-tight seal. In a preferred embodiment, barrels 100 and 106 are of different capacities and can accommodate various powder and liquid volumes. For example, one or both of the barrels of the mixing device into which the bone cement powder and liquid are added can be 1, 2, 3, 4, 5, 6, 7, 8, 9, or 10 cc, preferably 15, 20, 25, 30, 35, 40, 45, or 50 cc, more preferably 60, 70, 80, 90, or 100 cc, and most preferably 150, 200, 250, 300, 350, 400, 450, or 500 or more cc in volume. The device can be manufactured so that the barrels of the device hold the same volume or different volumes, and the barrels can be filled with the same or different volumes of components (e.g., bone cement powder or liquid). In preferred embodiments, the liquid (cc):powder (g) ratio is 0.1, 0.2, 0.3, 0.4, 0.5, 0.6, 0.7, 0.8, 0.9, 1, and 1.5:1, preferably 2, 3, 4, 5, 6, 7, 8, 9, or 10:1, more preferably 15, 20, 25, 30, 35, 40, 45, or 50:1 or more.

Operation

Referring to FIG. 1, the mixing device includes barrel 100, which is filled with calcium phosphate powder 101, and piston/plunger 102, which is inserted into barrel 100. Depressing piston/plunger 102 compresses the calcium phosphate powder to a desired density to reduce air content, facilitate wetting, and allow easy mixing. Barrel 100 also includes porous cap 112, which is attached at the distal end of barrel 100 to permit easy filling and compression. Porous cap 112 allows gas present in barrel 100 to vent when depressing piston/plunger 102 while retaining calcium phosphate powder 101 in barrel 100. Compression of the calcium phosphate powder in the device to 0.8 g/cc or less produces a poorly and ineffectively mixed paste following hydration. The same powder, when compressed to a density of 1.0 g/cc and hydrated, is effectively and uniformly wetted and mixed.

With reference to FIGS. 2 and 3, the mixing device also includes barrel 106, which is adapted to accept a needle, e.g., a 16 gauge needle, which is attached at the distal end of barrel 106. Liquid 110, e.g., USP saline, is drawn into barrel 106 through the needle by suction pressure by retracting piston/plunger 107. The needle is removed from the distal end of barrel 106 and barrel 106 is coupled to barrel 100 using Luer fittings 104 to form Luer connector 105. The saline is injected into calcium phosphate powder 101 by depressing piston/plunger 107, which injects the saline into barrel 100. After a brief delay to allow the liquid to wet the powder, air is vented by disconnecting barrel 100 from barrel 106 and slowly depressing the plungers. Barrel 100 and barrel 106 can be composed of clear polycarbonate to allow easy visualization during the venting step. Barrel 100 is reconnected to barrel 107 and mixing is performed by alternately and rapidly depressing pistons/plungers 102 and 107 several times until a uniform mixture (e.g., a paste) is formed (approximately 3-20 times). In the event not all material passes between barrel 100 and barrel 106, a series of alternating passes of plungers 107 and 102 can be performed until all material transfers and a uniform mixture is achieved. The narrow orifice that connects barrel 100 to barrel 106 increases shear, reduces agglomerates, and improves homogeneity and injectability of the mixture. After about 1 minute of mixing, the fully mixed paste is transferred into barrel 106, which is disconnected from barrel 100. A delivery needle or cannula (not shown) is attached to barrel 106 at Luer tip 104 and the cement can be fully extruded through the needle.

In at least some embodiments, the mixed material is injectable, i.e., capable of passing through a 7- to 18-gauge needle. The paste can also be prepared for delivery through a catheter (e.g., a catheter having a 7-15 gauge needle, and more preferably through a 7, 8, 9, 10, 11, 12, 13, 14, or 15 gauge needle).

Manufacture

Barrel 100 and piston/plunger 102 combine to form the powder syringe, while barrel 106 and piston/plunger 107 combine to form the delivery syringe, both of which can be obtained from various industry suppliers. Barrel 100 and barrel 106 can be independently manufactured from glass or plastic (e.g., polypropylene, polyethylene, polycarbonate, polystyrene, and the like). Pistons/Plungers 102 and 107 include a plastic or glass arm attached to stopper 102 and 108, respectively. Barrel 100 is filled with calcium phosphate powder 110 (e.g., any of the calcium phosphate powders described herein). Porous cap 112, which includes a porous polymer insert and a Luer connector, can be obtained from B. Braun (e.g., SAFSITE® Capped Valve System; ULTRASITE® Capless Valve System).

The mixing device can also include a standard hypodermic needle, which can be obtained from various industry suppliers.

In an embodiment, the powder syringe is placed into a moisture barrier tray along with a silica gel desiccant canister (e.g., a thermoformed tray inside a foil pouch may be used or a moisture barrier tray formed from a poly(ester) copolymer of terephthalic acid, ethylene glycol and cyclohexane dimethanol known as "PETG" can be used; see, e.g., U.S. Pat. No. 4,284,671; incorporated herein by reference). This moisture barrier configuration preserves the product (i.e., the calcium phosphate powder) by allowing moisture transmission through the porous cap so that it can be absorbed into the desiccant; the device design is particularly effective at elevated temperatures which would normally lead to cement degradation. The cement composition within the mixing device was degraded within 2 weeks at 50° C. without desiccant, but was intact after 4 months with desiccant.

The invention is illustrated by the following examples, which are not intended to be limiting of the invention.

EXAMPLES

Example 1

In order to determine the optimum compaction for a calcium phosphate powder, fifteen 20 mL mixing devices (syringes) with porous caps were each filled with 6.0 grams of calcium phosphate. The plungers were inserted into the barrel and compressed using a uniaxial testing machine until a given powder density was achieved. Three syringes were compressed to each of the following densities; 0.75, 0.86, 1.0, 1.1, 1.2 g/cc. Syringes were then tested by hydrating with 3.0 cc of saline using a 10 mL syringe and mixed by passing the powder and saline back and forth between the syringes until a smooth paste was achieved. The number of passes, or strokes, required to achieve complete mixing was recorded and averaged for each density. The results are shown in FIG. 4. A powder density of 1.0 g/cc was found to be optimal for this calcium phosphate.

Example 2

To demonstrate the ability of the present device and its method of use to simplify preparation and to enhance injectability of a conventional calcium phosphate cement (CPC) the following study was performed.

Two CPC precursors; an amorphous calcium phosphate (ACP) (with Ca/P<1.5) and dicalcium phosphate dihydrate (DCPD) seeded with apatite (10-25% w/w) were prepared using a low temperature double decomposition technique. The two powders were mixed at a 1:1 ratio and milled in a high-energy ball mill for 3 hours. The resulting powder was filled into a syringe and connected to a second syringe filled with saline by means of a luer connector. The saline was injected into the powder at a liquid to powder (L/P) ratio of 0.5:1 and the mixture was then passed back-and-forth between the syringes until a uniform paste was formed (approximately 5 passes). The same cement mixed (with the same L/P) in a bowl with a spatula and then transferred into a syringe was used as a control. The materials were tested for chemical composition (FT-IR, XRD, and Ca:P atomic ratio) and performance characteristics (injection force and yield, working time, hardening rate, compressive strength, and resistance to washout).

Syringe mixing reduced preparation time from two minutes to one minute, and the cement was deliverable through a 16 gauge needle with less than 3 kgf force. A 50% reduction in injection force relative to bowl mixed materials was observed. Syringe mixing also increased the percentage of CPC delivered. The delivered amount was less than 90% for bowl mixed cement but was 100% for syringe mixed cement. Syringe mixed cement could be stored for up to 6 minutes at room temperature and remixed while retaining full injectability. The mixing did not affect the hardening rate, compressive strength, or resistance to washout of the CPC, nor did it change the chemical composition. The injectable cement hardened in less than 5 minutes at 37° C., achieved a compressive strength of 30 MPa in 2 hours and could be injected directly into a water bath without loss of material.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A bone cement mixing and delivery system comprising:
a first rigid tube comprising a first body having a constant inner diameter and a first tip having a smaller inner diameter than the inner diameter of the first body, and a first movable piston comprising a first rubber stopper at a terminal end thereof, the first rubber stopper having an outer diameter that is the same as the constant inner diameter of the first body, the first movable piston configured to be inserted rubber stopper-first into the first body of the first rigid tube opposite the first tip and prevent leakage of contents from the first rigid tube;
a calcium phosphate bone cement powder, the first rigid tube is filled with a quantity of the calcium phosphate bone cement powder therein;
a luer connector removably attached to the first tip;
a porous cap configured to be removeably attached to the first tip of said first rigid tube via the luer connector, wherein said porous cap is configured to permit venting of gas, but not said calcium phosphate bone cement powder, from said first rigid tube; and
a second rigid tube comprising a second body having a constant inner diameter and a second tip having a smaller inner diameter than the inner diameter of the second body, and a second movable piston comprising a second rubber stopper at a terminal end thereof, the second rubber stopper having an outer diameter that is the same as the constant inner diameter of the second body, the second movable piston configured to be inserted rubber stopper-first into the second body of the second rigid tube opposite the second tip and prevent leakage of contents from the second rigid tube;
wherein said first rigid tube is configured to be joined tip-to-tip to said second rigid tube via the Luer connector such that, when joined, there is fluid communication between the tubes and an interior space is formed comprising an interior of the first rigid tube between the first rubber stopper of the first movable piston and the first tip of the first rigid tube and an interior of the second rigid tube between the second rubber stopper of the second movable piston and the second tip of the second rigid tube that is leak-tight against liquid at the time of the joining and throughout the joining, wherein the system is configured such that removable attachment of the porous cap to the tip of the first rigid tube via the luer connector and pressing of the movable piston of the first rigid tube and venting of gas but not the calcium phosphate bone cement powder from the first rigid tube forms a compressed calcium phosphate bone cement powder having a density of about 1.0 g/cc.

2. The system of claim 1, wherein said first and second rigid tubes and movable pistons comprise disposable syringes.

3. The system of claim 1, wherein said second tube is filled with a physiologically acceptable fluid, such that after said first and second tubes are joined tip-to-tip the first and second tubes are configured for mixing said calcium phosphate bone cement powder by alternate depressions of the pistons of the first and second tubes.

4. The system of 3, wherein said system comprises a ratio of the physiologically acceptable fluid to the quantity of the calcium phosphate bone cement powder of 0.1:1 to 50:1.

5. The system of claim 3, wherein said physiologically acceptable fluid is selected from water, saline, a phosphate buffer, and a biological fluid.

6. A kit comprising the system of claim 1 and moisture barrier packaging enclosing at least the calcium phosphate bone cement powder.

7. The kit of claim 6, wherein said kit further comprises a desiccant.

8. The kit of claim 7, wherein the kit comprises a rigid or flexible container with a permeable barrier layer separating at least the calcium phosphate bone cement powder from the desiccant.

9. The system of claim 1,
wherein the first movable piston that is configured to fit in the first rigid tube is inserted in a proximal end of said first rigid tube, and the porous cap is removeably attached by the Luer connector to a distal end of said first rigid tube.

10. The system of claim 1, wherein the calcium phosphate bone cement powder comprises amorphous calcium phosphate.

11. The system of claim 1, wherein the calcium phosphate bone cement powder comprises amorphous calcium phosphate and dicalcium phosphate dihydrate.

* * * * *